(12) United States Patent
Kofukuda et al.

(10) Patent No.: US 7,781,603 B2
(45) Date of Patent: Aug. 24, 2010

(54) METHOD FOR PRODUCING TRIMETHYLSILYL AZIDE

(75) Inventors: Toru Kofukuda, Hyogo (JP); Shigeto Nakazawa, Hyogo (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 92 days.

(21) Appl. No.: 11/576,095

(22) PCT Filed: Mar. 25, 2005

(86) PCT No.: PCT/JP2005/006449

§ 371 (c)(1),
(2), (4) Date: Mar. 27, 2007

(87) PCT Pub. No.: WO2006/038329

PCT Pub. Date: Apr. 13, 2006

(65) Prior Publication Data

US 2008/0058540 A1 Mar. 6, 2008

(30) Foreign Application Priority Data

Sep. 30, 2004 (JP) ............................. 2004-317169

(51) Int. Cl.
*C07F 7/10* (2006.01)
*C07B 61/00* (2006.01)

(52) U.S. Cl. ........................................................ 552/4

(58) Field of Classification Search ........................ None
See application file for complete search history.

(56) References Cited

FOREIGN PATENT DOCUMENTS

| JP | 63-23386 | 2/1985 |
| JP | 1-143878 | 6/1989 |
| JP | 6-65260 | 3/1994 |
| JP | 10-45769 | 2/1998 |

OTHER PUBLICATIONS

Du et al. Journal of Chemical Research, (Mar. 2004) 223-225.*
Nishiyama and Yamaguchi, "Selective Formation of Alkyl Azides Using Trimethylsilyl Azide and Carbonyl Compounds," Synthesis 2:106-108, 1988.
Birkofer and Wegner, "Trimethylsilyl Azide," Organic Synthesis 50:1030-1033, 1970.
West and Thayer, "Organosilyl Azides," J. Amer. Chem. Soc. 84:1763-1764, 1962.
Sukata, "Efficient Synthesis of Silyl Azides Using Sodium Azide Impregnated on Amberlite XAD Resin," J. Org. Chem. 53(20):4867-4869, 1988.

* cited by examiner

*Primary Examiner*—Daniel M Sullivan
*Assistant Examiner*—Yevegeny Valenrod
(74) *Attorney, Agent, or Firm*—Fish & Richardson P.C.

(57) ABSTRACT

The present invention relate to a method for producing a trimethylsilyl azide represented by the formula (3):

$$(CH_3)_3SiN_3 \qquad (3)$$

which comprises reacting a trimethylsilyl chloride represented by the formula (1):

$$(CH_3)_3SiCl \qquad (1)$$

with an inorganic salt of hydrogen azide represented by the formula (2):

$$M(N_3)_n \qquad (2)$$

wherein M represents an alkali metal or an alkaline earth metal, and n represents 1 or 2, in the presence of a phase-transfer catalyst and an organic solvent having a high boiling point.

18 Claims, No Drawings

METHOD FOR PRODUCING TRIMETHYLSILYL AZIDE

CROSS REFERENCE TO RELATED APPLICATIONS

The present application is a national phase application under 35 U.S.C. §371 of International Patent Application PCT/JP2005/006449, filed Mar. 25, 2005, which claims priority to Japanese Patent Application Serial No. 2004-317169, filed Sep. 30, 2004. The contents of the prior applications are incorporated herein by reference in their entirety.

TECHNICAL FIELD

The present invention relates to a method for producing trimethylsilyl azide useful for synthesis of an aminating agent, an azidating agent or a heterocyclic compound.

BACKGROUND ART

Heretofore, as a method for producing trimethylsilyl azide, a method in which trimethylsilyl chloride and an inorganic salt of hydrogen azide are reacted in a solvent having a low boiling point such as di-n-butyl ether or diethylene glycol dimethyl ether or bis(2-methoxyethyl)ether has been known (see Non-patent documents 1, 2 and 3).

Further, a method in which trimethylsilyl chloride and an inorganic salt of hydrogen azide carried on a macroporous polymer are reacted in a solvent such as decalin, acetonitrile or dichloromethane has been also known (see Patent document 1 and Non-patent document 4).

Furthermore, a method in which synthesis is carried out using trimethylsilyl chloride and an inorganic salt of hydrogen azide in the absence of a solvent has been reported (see Patent document 2).

However, in the above production methods, there are the following problems (1) to (4).

(1) In the synthesis method using a solvent having a low boiling point, a long time of 48 hours to 60 hours is required until the reaction is completed. Further, in order to shorten the reaction time, it is necessary to use an inorganic salt of hydrogen azide which is carried on a macroporous polymer.

(2) As a method of isolating the resulting trimethylsilyl azide, there is only a method by distillation. In the distillation, trimethylsilyl azide and a solvent are not sufficiently separated, and the solvent is contaminated in trimethylsilyl azide, whereby the purity thereof is decreased. Namely, in order to obtain trimethylsilyl azide with high purity, a multistage precision distillation apparatus is required and therefore equipment therefor is required, which results in increasing the production cost.

(3) In the case where synthesis is carried out in the absence of a solvent, the above problems may be solved. However, there are problems that the load upon starting stirring is extremely large, which imposes the load on the apparatus, that a large amount of heat generation occurs all at once in the initial stage of the reaction, and the like.

(4) The trimethylsilyl azide thus produced can be isolated to high purity only by a simple distillation without resort to a multistage precision distillation apparatus. However, since a solvent is not used, byproduct salts are not dispersed, and therefore, as the distillation procedure is getting closer to the final stage, it becomes more difficult to carry out stirring.

Patent document 1: JP-A-1-143878
Patent document 2: JP-A-10-45769
Non-patent document 1: Synthesis, 2, 106-107 (1988)
Non-patent document 2: Org. Synth., 50, 107 (1970)
Non-patent document 3: J. Amer. Chem. Soc. 84, 1763, (1962)
Non-patent document 4: J. Org. Chem. 53, 20, 4867-4869, (1988)

DISCLOSURE OF THE INVENTION

Problems that the Invention is to Solve

An object of the present invention is to solve the above problems of the conventional art and to provide a method for easily and safely producing trimethylsilyl azide having high quality in high yield using trimethylsilyl chloride.

In order to achieve the above object, the present inventors made intensive studies and found that trimethylsilyl azide can be industrially, safely and efficiently produced by using an organic solvent having a high boiling point in the presence of a phase-transfer catalyst, and thus the present invention has been achieved.

That is, the present invention relates to the followings.

[1] A method for producing a trimethylsilyl azide represented by the formula (3):

$$(CH_3)_3 SiN_3 \qquad (3)$$

which comprises reacting a trimethylsilyl chloride represented by the formula (1):

$$(CH_3)_3SiCl \qquad (1)$$

with an inorganic salt of hydrogen azide represented by the formula (2):

$$M(N_3)_n \qquad (2)$$

wherein M represents an alkali metal or an alkaline earth metal, and n represents 1 or 2, in the presence of a phase-transfer catalyst and an organic solvent having a high boiling point.

[2] The method according to [1] above, wherein the organic solvent having a high boiling point is silicone oil or liquid paraffin.

[3] The method according to [1] above, wherein the organic solvent having a high boiling point is dodecane, tridecane, tetradecane, pentadecane, hexadecane, heptadecane or octadecane.

[4] The method according to any one of [1] to [3] above, wherein the inorganic salt of hydrogen azide is sodium azide.

[5] The method according to any one of [1] to [4] above, wherein the phase-transfer catalyst is polyethylene glycol or silylated polyethylene glycol.

Advantage Of The Invention

The present invention is directed to a method which is very useful for safely producing trimethylsilyl azide with high purity without imposing a load on the apparatus in a shorter time reaction, in comparison with conventional methods in which a solvent having a low boiling point is used or in which synthesis is carried out in the absence of a solvent.

Best Mode For Carrying Out The Invention

Specific examples of the organic solvent having a high boiling point that can be used in the production method of the present invention include liquid paraffin, silicone, silicone oil, hexane, heptane, octane, nonane, decane, undecane, dodecane, tridecane, tetradecane, pentadecane, hexadecane, heptadecane, octadecane, nonadecane, and eicosane, while it is not limited thereto. Preferred examples thereof are silicone oil, dodecane, tridecane, tetradecane, pentadecane, hexadecane, heptadecane and octadecane, which are industrially suitable.

Specific examples of the inorganic salt of hydrogen azide that can be used in the production method of the present invention include azides of alkali metals or alkaline earth metals such as sodium, potassium, lithium, calcium and magnesium. Preferred example thereof is sodium azide, which is industrially suitable. The use amount of such an inorganic salt of hydrogen azide is in the range of from 1.0 to 1.5 mol, preferably from 1.0 to 1.05 mol in terms of hydrogen azide, with respect to 1 mol of trimethylsilyl chloride.

As a specific example of the phase-transfer catalyst that can be used in the production method of the present invention, a conventionally known quaternary ammonium salt, a tertiary amine which can act as a source of quaternary ammonium, or a polyether compound can be used. Examples thereof include tetraethylammonium bromide, tetrabutylammonium bromide, hexadecyltributylammonium bromide, methyltrioctylammonium chloride, triethylamine hydrochloride, polyethylene glycol methyl ether, polyethylene glycol tetrahydrofurfuryl ether, polyethylene glycol distearate, and polyethylene glycol; and silylated polyethylene glycol methyl ether, silylated polyethylene glycol tetrahydrofurfuryl ether, and silylated polyethylene glycol, while it is not limited thereto. Preferred examples thereof are polyethylene glycol and silylated polyethylene glycol since they are industrial and inexpensive. The use amount of such a phase-transfer catalyst is generally 0.1% by weight or more, preferably in the range of from 1 to 6% by weight with respect to trimethylsilyl chloride.

As for the reaction, the reaction can be carried out after the inorganic salt of hydrogen azide, solvent, catalyst and trimethylsilyl chloride are fed at the same time. However, it is preferred that the solvent is fed in advance, and the inorganic salt of hydrogen azide, catalyst and trimethylsilyl chloride are then fed thereto. By doing so, the load upon starting stirring can be reduced, and further, by controlling the addition rate, the heat generation accompanying the reaction can be controlled.

The reaction temperature is generally in the range of from 0 to 70° C., preferably from 45 to 60° C. Although the reaction time is affected by the addition amount of the catalyst and the reaction temperature, it is generally in the range of from 0.5 to 20 hours, preferably from 1 to 10 hours.

Isolation of trimethylsilyl azide with high purity after completion of the reaction can be carried out by distillation. Since the organic solvent having a high boiling point is used, it is possible to conduct the isolation by only simple distillation without requiring a multistage precision distillation apparatus. Moreover, due to the presence of the solvent, byproduct salts can be dispersed, and therefore, stirring can be easily carried out until distillation is completed.

EXAMPLES

The present invention will be more specifically described with reference to the following Examples. However, the invention is not limited to these Examples.

Example 1

To a flask equipped with a reflux condenser, a thermometer and a stirrer, 250 ml of silicone oil (TSF458-100, GE Toshiba Silicone Co., Ltd.), 77.0 g (1.2 mol) of sodium azide and 2.5 g of polyethylene glycol were fed, the mixture was heated to 50 to 59° C., and 125.0 g (1.2 mol) of trimethylsilyl chloride was added dropwise thereto. After completion of the dropwise addition, the reaction was allowed to proceed at 59° C. for 2 hours. After completion of the reaction, the inner temperature was raised to 105° C. by heating, and trimethylsilyl azide was isolated by simple distillation. Also after the completion of the distillation, byproduct salts could be dispersed, and stirring could be easily carried out. As a result, 128.5 g (1.1 mol) of trimethylsilyl azide was obtained as a clear and colorless liquid. This amount corresponds to a yield of 96.9% relative to trimethylsilyl chloride. Further, the purity thereof by a gas chromatography (GC) analysis was 97.9%.

Example 2

To the same apparatus as in Example 1, 50 ml of n-tetradecane, 15.4 g (0.2 mol) of sodium azide and 0.3 g of polyethylene glycol were fed, the mixture was heated to 50 to 54° C., and 25.0 g (0.2 mol) of trimethylsilyl chloride was added dropwise thereto. After completion of the dropwise addition, the reaction was allowed to proceed at 54 to 61° C. for 3 hours. After completion of the reaction, the inner temperature was raised to 105 to 112° C. by heating, and trimethylsilyl azide was isolated by simple distillation. Also after the completion of the distillation, byproduct salts could be dispersed, and stirring could be easily carried out. As a result, 24.3 g (0.2 mol) of trimethylsilyl azide was obtained as a clear and colorless liquid. This amount corresponds to a yield of 91.5% relative to trimethylsilyl chloride. Further, the purity thereof by a gas chromatography (GC) analysis was 94.3%.

Example 3

To the same apparatus as in Example 1, 50 ml of n-hexadecane, 15.4 g (0.2 mol) of sodium azide and 0.3 g of polyethylene glycol were fed, the mixture was heated to 50 to 57° C., and 25.0 g (0.2 mol) of trimethylsilyl chloride was added dropwise thereto. After completion of the dropwise addition, the reaction was allowed to proceed at 60 to 62° C. for 3 hours. After completion of the reaction, the inner temperature was raised to 105 to 116° C. by heating, and trimethylsilyl azide was isolated by simple distillation. Also after the completion of the distillation, byproduct salts could be dispersed, and stirring could be easily carried out. As a result, 24.6 g (0.2 mol) of trimethylsilyl azide was obtained as a clear and colorless liquid. This amount corresponds to a yield of 92.9% relative to trimethylsilyl chloride. Further, the purity thereof by a gas chromatography (GC) analysis was 96.1%.

Example 4

To the same apparatus as in Example 1, 50 ml of n-octadecane, 15.4 g (0.2 mol) of sodium azide and 0.3 g of polyethylene glycol were fed, the mixture was heated to 50 to 54° C., and 25.0 g (0.2 mol) of trimethylsilyl chloride was added dropwise thereto. After completion of the dropwise addition, the reaction was allowed to proceed at 62 to 63° C. for 3 hours. After completion of the reaction, the inner temperature was raised to 103 to 115° C. by heating, and trimethylsilyl azide was isolated by simple distillation. Also after the completion of the distillation, byproduct salts could be dispersed, and stirring could be easily carried out. As a result, 24.7 g (0.2 mol) of trimethylsilyl azide was obtained as a clear and colorless liquid. This amount corresponds to a yield of 93.2% relative to trimethylsilyl chloride. Further, the purity thereof by a gas chromatography (GC) analysis was 96.6%.

Example 5

To the same apparatus as in Example 1, 50 ml of liquid paraffin, 15.4 g (0.2 mol) of sodium azide and 0.3 g of polyethylene glycol were fed, the mixture was heated to 50 to 53° C., and 25.0 g (0.2 mol) of trimethylsilyl chloride was added dropwise thereto. After completion of the dropwise addition, the reaction was allowed to proceed at 60 to 64° C. for 3 hours. After completion of the reaction, the inner temperature was raised to 95 to 112° C. by heating, and trimethylsilyl azide was isolated by simple distillation. Also after the completion of the distillation, byproduct salts could be dispersed, and stirring could be easily carried out. As a result, 24.4 g (0.2 mol) of trimethylsilyl azide was obtained as a clear and colorless liquid. This amount corresponds to a yield of 92.0% relative to trimethylsilyl chloride. Further, the purity thereof by a gas chromatography (GC) analysis was 96.3%.

The invention claimed is:

1. A method for producing a trimethylsilyl azide represented by the formula (3):

$$(CH_3)_3SiN_3 \quad (3)$$

which comprises reacting a trimethylsilyl chloride represented by the formula (1):

$$(CH_3)_3SiCl \quad (1)$$

with an inorganic salt of hydrogen azide represented by the formula (2):

$$M(N_3)_n \quad (2)$$

wherein M represents an alkali metal or an alkaline earth metal, and n represents 1 or 2, in the presence of a composition consisting of a phase-transfer catalyst and an organic solvent selected from the group consisting of silicon oil, liquid paraffin, dodecane, tridecane, tetradecane, pentadecane, hexadecane, heptadecane, and octadecane.

2. The method according to claim 1, wherein the inorganic salt of hydrogen azide is sodium azide.

3. The method according to claim 1, wherein the phase-transfer catalyst is polyethylene glycol or silylated polyethylene glycol.

4. A method for producing a trimethylsilyl azide represented by the formula (3):

$$(CH_3)_3SiN_3 \quad (3)$$

which comprises reacting a trimethylsilyl chloride represented by the formula (1):

$$(CH_3)_3SiCl \quad (1)$$

with an inorganic salt of hydrogen azide represented by the formula (2):

$$M(N_3)_n \quad (2)$$

wherein M represents an alkali metal or an alkaline earth metal, and n represents 1 or 2, in the presence of a composition consisting of a phase-transfer catalyst and an organic solvent;
wherein the organic solvent is a non-polar organic solvent having a boiling point of dodecane or higher.

5. The method according to claim 4, wherein the organic solvent is silicone oil or liquid paraffin.

6. The method according to claim 4, wherein the organic solvent is dodecane, tridecane, tetradecane, pentadecane, hexadecane, heptadecane or octadecane.

7. The method according to claim 4, wherein the inorganic salt of hydrogen azide is sodium azide.

8. The method according to claim 4, wherein the phase-transfer catalyst is polyethylene glycol or silylated polyethylene glycol.

9. The method according to claim 4, further comprising isolating the trimethylsilyl azide by a simple distillation.

10. The method according to claim 1, further comprising isolating the trimethylsilyl azide by a simple distillation.

11. A method for producing a trimethylsilyl azide represented by the formula (3):

$$(CH_3)_3SiN_3 \quad (3),$$

the method comprising:
reacting a trimethylsilyl chloride represented by the formula (1):

$$(CH_3)_3SiCl \quad (1)$$

with an inorganic salt of hydrogen azide represented by the formula (2):

$$M(N_3)_n \quad (2); \text{ and}$$

isolating the trimethylsilyl azide by a simple distillation;
wherein M represents an alkali metal or an alkaline earth metal, and n represents 1 or 2, in the presence of a phase-transfer catalyst and an organic solvent selected from the group consisting of silicon oil, liquid paraffin, dodecane, tridecane, tetradecane, pentadecane hexadecane, heptadecane, and octadecane.

12. The method according to claim 11, wherein the inorganic salt of hydrogen azide is sodium azide.

13. The method according to claim 11, wherein the phase-transfer catalyst is polyethylene glycol or silylated polyethylene glycol.

14. A method for producing a trimethylsilyl azide represented by the formula (3):

$$(CH_3)_3SiN_3 \quad (3),$$

the method comprising:
reacting a trimethylsilyl chloride represented by the formula (1):

$$(CH_3)_3SiCl \quad (1)$$

with an inorganic salt of hydrogen azide represented by the formula (2):

$$M(N_3)_n \quad (2); \text{ and}$$

isolating the trimethylsilyl azide by a simple distillation;
wherein M represents an alkali metal or an alkaline earth metal, and n represents 1 or 2, in the presence of a phase-transfer catalyst and an organic solvent;
wherein the organic solvent is a non-polar organic solvent having a boiling point of dodecane or higher.

15. The method according to claim 14, wherein the organic solvent is silicone oil or liquid paraffin.

16. The method according to claim 14, wherein the organic solvent is dodecane, tridecane, tetradecane, pentadecane, hexadecane, heptadecane or octadecane.

17. The method according to claim 14, wherein the inorganic salt of hydrogen azide is sodium azide.

18. The method according to claim 14, wherein the phase-transfer catalyst is polyethylene glycol or silylated polyethylene glycol.

* * * * *